US012734071B2

(12) United States Patent
Li et al.

(10) Patent No.: US 12,734,071 B2
(45) Date of Patent: Sep. 15, 2026

(54) EYE MASK AND CONTROL METHOD

(71) Applicant: Shenzhen Rainslab Technology Co., Ltd, Shenzhen (CN)

(72) Inventors: Cihang Li, Shenzhen (CN); Jinhui Ma, Shenzhen (CN)

(73) Assignee: Shenzhen Rainslab Technology Co., Ltd, Shenzhen (CN)

( * ) Notice: Subject to any disclaimer, the term of this patent is extended or adjusted under 35 U.S.C. 154(b) by 501 days.

(21) Appl. No.: 18/481,357

(22) Filed: Oct. 5, 2023

(65) Prior Publication Data

US 2024/0173171 A1 May 30, 2024

(30) Foreign Application Priority Data

Nov. 24, 2022 (CN) ......................... 202211485150.7
Feb. 28, 2023 (CN) ......................... 202320423271.2

(51) Int. Cl.
*A61F 9/04* (2006.01)
*A61M 21/02* (2006.01)
*A61M 21/00* (2006.01)

(52) U.S. Cl.
CPC ............... *A61F 9/04* (2013.01); *A61M 21/02* (2013.01); *A61M 2021/0022* (2013.01); *A61M 2021/005* (2013.01); *A61M 2021/0066* (2013.01); *A61M 2021/0088* (2013.01); *A61M 2205/584* (2013.01); *A61M 2205/587* (2013.01); *A61M 2209/088* (2013.01)

(58) Field of Classification Search
CPC ..... A61M 21/00–02; A61M 2210/0612; A61F 9/04–045; A61H 2205/024
See application file for complete search history.

(56) References Cited

U.S. PATENT DOCUMENTS

2007/0002692 A1* 1/2007 Van Brunt ........... G04G 13/021 368/79
2015/0209597 A1* 7/2015 Haarlander ............ A61H 23/02 607/90
2018/0133059 A1* 5/2018 Hardi ................... H04R 1/1008
2021/0015659 A1* 1/2021 Lau ........................... A61F 9/04
2022/0054867 A1* 2/2022 Adams ............... B01D 46/0086

FOREIGN PATENT DOCUMENTS

CN 115089376 A * 9/2022 ............. A61F 9/045

* cited by examiner

*Primary Examiner* — Thaddeus B Cox

(57) ABSTRACT

An eye mask and a control method thereof are provided. The eye mask includes a casing, a first information prompting device and a second information prompting device arranged on the casing. The first information prompting device is configured for internally giving information prompts, the second information prompting device is configured for externally giving information prompts. The control method includes controlling the first information prompting device and the second information prompting device to give information prompts simultaneously in a working state.

15 Claims, 8 Drawing Sheets controlling the first information prompting device and the second information prompting device to give information prompts simultaneously

↓

Figure 6:
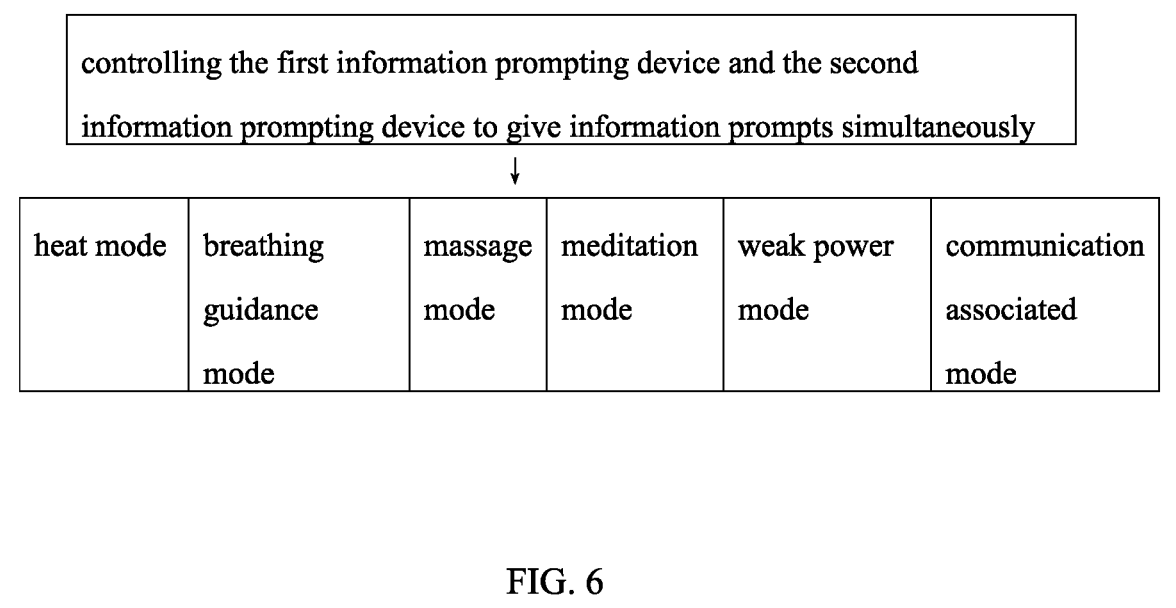

| heat mode | breathing guidance mode | massage mode | meditation mode | weak power mode | communication associated mode |
|---|---|---|---|---|---|

FIG. 6 controlling the first illuminant and the second illuminant to emit light simultaneously

Figure 7:
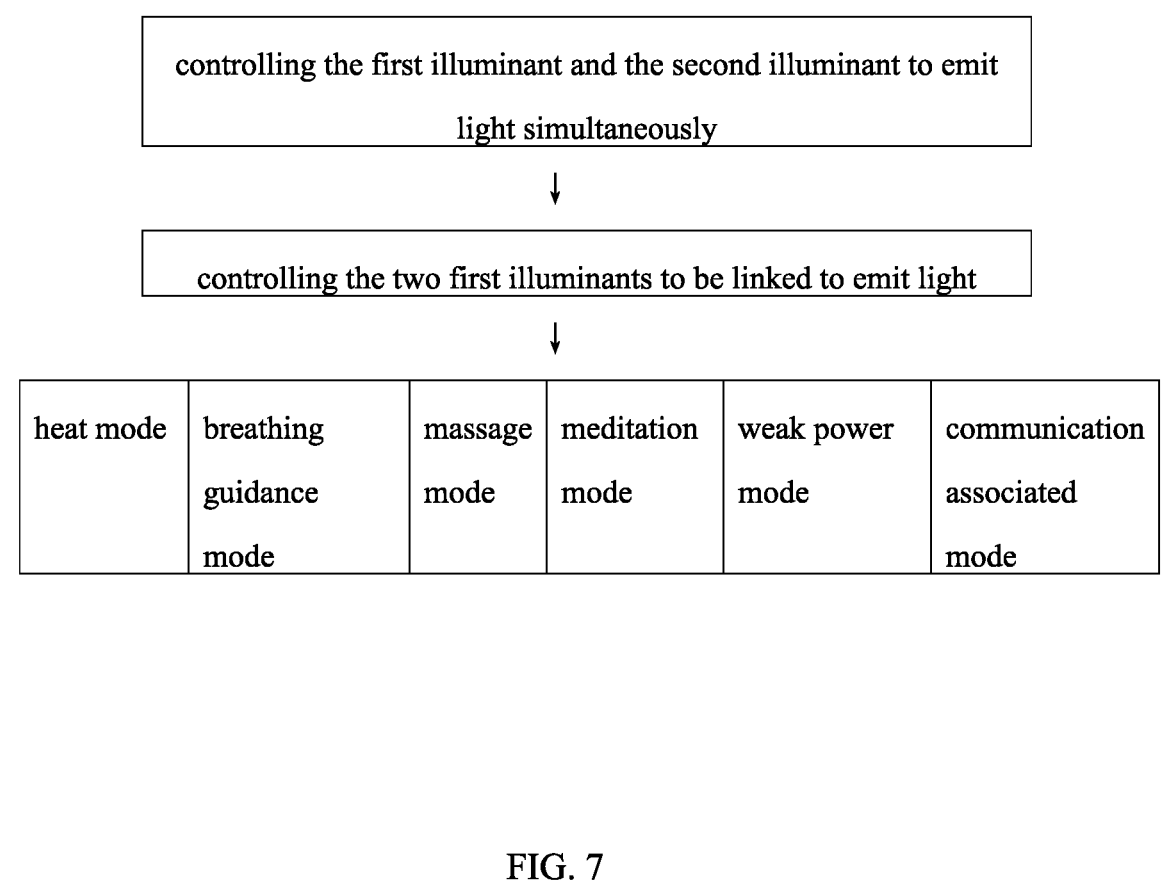

↓ controlling the two first illuminants to be linked to emit light

↓

| heat mode | breathing guidance mode | massage mode | meditation mode | weak power mode | communication associated mode |
|---|---|---|---|---|---|

FIG. 7 controlling an intensity and/or a color of the light emitted by the two first illuminants to change, and to present a periodic change rule related to a working rule of the massage vibrator

↓

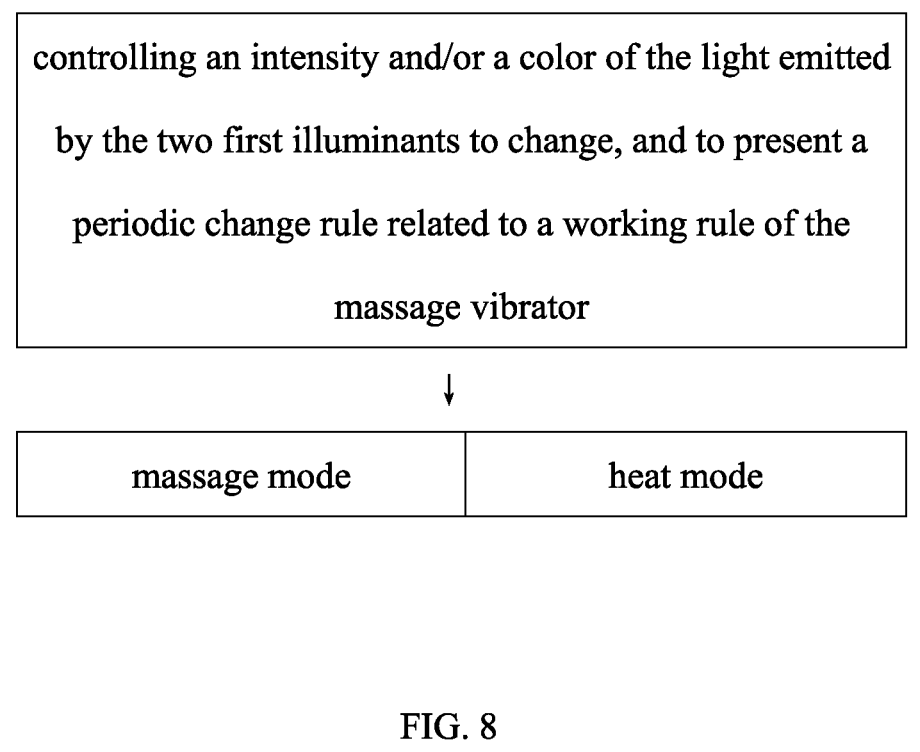

| massage mode | heat mode |
|---|---|

FIG. 8

EYE MASK AND CONTROL METHOD

FIELD OF THE INVENTION

The present invention relates to a medical care field, in particular to an eye mask and a control method thereof.

BACKGROUND OF THE INVENTION

With the continuous acceleration of urbanization, people's living standards continue to improve, but at the same time, the acceleration of the pace of life also makes the competition among people increasingly fierce. Studies have shown that once a person is in a high pressure environment for a long time, it is easy to cause insomnia, dreaminess, inattention, etc., and what's more, neurasthenia, or depression. Insomnia and depression can cause a variety of physical and psychological diseases in people. Therefore, timely and effective relief of physical and mental fatigue, and targeted physical therapy for insomnia and other crux are particularly important for improving people's living conditions.

Eye masks help to improve insomnia, but traditional eye masks do not remind others that users are in a certain state, or remind users that they are in a certain state, which cannot meet people's diverse and intelligent needs.

SUMMARY OF THE INVENTION

In view of the above reasons, the object of the present invention is to provide an eye mask and its control method, which has the function of prompting or interaction, which is achieved through the following technical solutions:

In a first aspect, an eye mask includes a casing, a first information prompting device, a second information prompting device arranged on the casing and a controller. The first information prompting device is configured for internally giving information prompts, the second information prompting device is configured for externally giving information prompts. The controller is configured for controlling the first information prompting device and the second information prompting device to give information prompts simultaneously in a working state.

In a second aspect, a control method of the eye mask includes controlling the first information prompting device and the second information prompting device to give information prompts simultaneously.

The control method of the eye mask uses the external information prompting device to remind others, for example, public people or a teacher that the user wearing the eye mask is in a certain working state, for example, he may be in the state of breathing physiotherapy, meditation or single massage or hot compress, and uses the internal information prompting device to also remind the user in what certain working state, so the eye mask has interaction with others or the user himself. The eye mask of the present invention meets people's control needs such as humanization and intelligence by using light combination.

BRIEF DESCRIPTION OF THE DRAWINGS

The accompanying drawings are used to provide a further understanding of the present invention, and constitute a part of the description, and are used to explain the present invention together with the embodiments of the present invention, and do not constitute a limitation to the utility model. In the attached drawings:

FIG. 6 is a schematic diagram of a working mode control of the working state of the eye mask according to an embodiment of the present invention.

FIG. 7 is another schematic diagram of a working mode control of the working state of the eye mask according to another embodiment of the present invention.

FIG. 8 is a further schematic diagram of a working mode control of the working state of the eye mask according to further another embodiment of the present invention.

DETAILED DESCRIPTION OF PREFERRED EMBODIMENTS

In order to have a clearer understanding of the technical features, purposes and beneficial effects of the present invention, the technical solution of the present invention is described in detail below, but it should not be construed as limiting the scope of implementation of the present invention. Based on the embodiments of the present invention, all other embodiments obtained by persons of ordinary skill in the art without making creative efforts belong to the protection scope of the present invention.

Figure 1:
FIG. 1 is a schematic perspective view of an eye mask showing an outer surface thereof according to an embodiment of the present invention.
Figure 1:
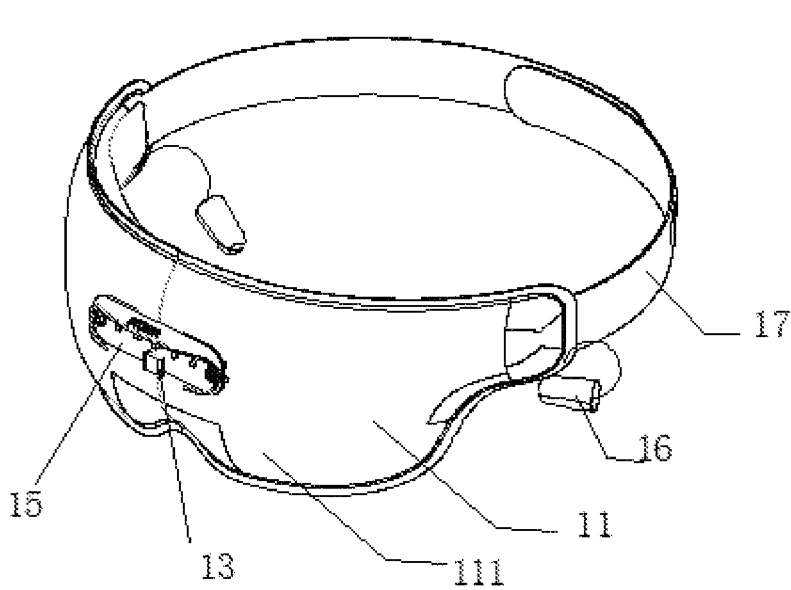
Figure 2:
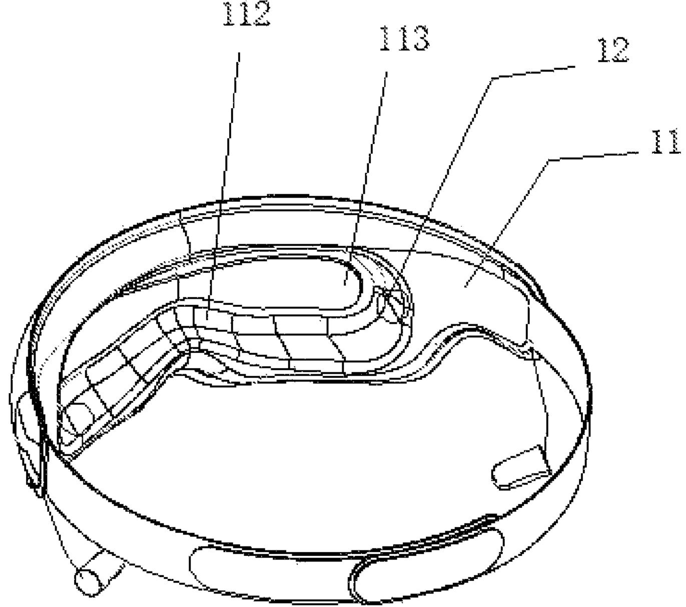
FIG. 2 is another schematic perspective view of an eye mask showing an inner surface thereof according to the embodiment of the present invention.

The embodiment of the present application provides a method for controlling an eye mask 100, please refer to FIGS. 1-2, the eye mask 100 basically includes a casing 11 for covering the eyes, and a first information prompting device and a second information prompting device disposed on the casing 11. The first information prompting device is configured for internally giving information prompts. The second information prompting device is configured for externally giving information prompts. In a working state, the first information prompting device and the second information prompting device issue information prompts simultaneously.

The second information prompt device can be one or two combinations of LCD screen, laser light, LED light, and projection screen, with the basic function of reminding others that the user wearing the eye mask is in a certain working state, for example, when multiple people are meditating, the teacher can guide the students wearing the eye mask to meditate together through the state of the second information prompt device; and another example, it is beneficial for others not to easily disturb the users.

The first information prompting device can also be one of liquid crystal screen, laser lamp, LED lamp, and projection screen or a combination thereof. In present embodiment, it mainly includes two first illuminants 12, which are located in the inner surface 112 of the casing 11, preferably, the two first illuminants 12 are symmetrically distributed on both sides of the casing 11 and substantially corresponding to the positions of the eyes. The casing 11 can be provided with inner recesses 113 at the positions corresponding to the eyes, so that there is a space distance from each of the eyes, which is more comfortable for users. The casing 11 can be made of memory foam material, so that it has a more shaping and supporting effect. The first illuminants 12 can be arranged on the sides of the inner recesses 113.

Figure 3:
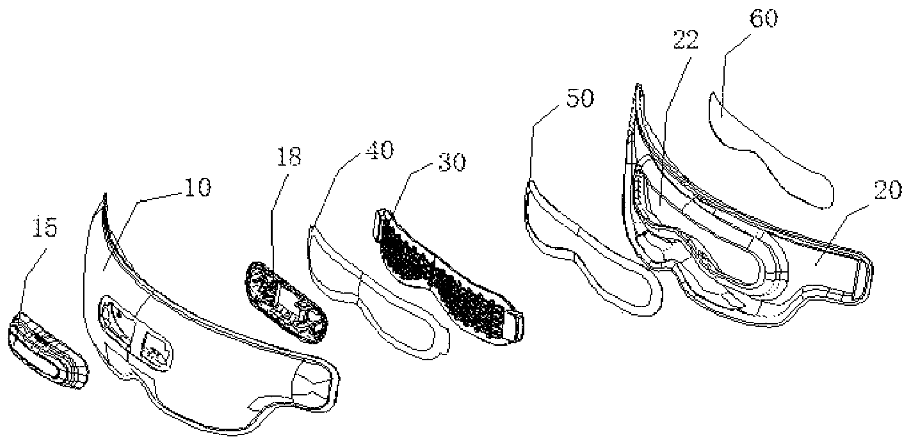
FIG. 3 is a partial exploded view of the eye mask according to the embodiment of the present invention.
Figure 4:
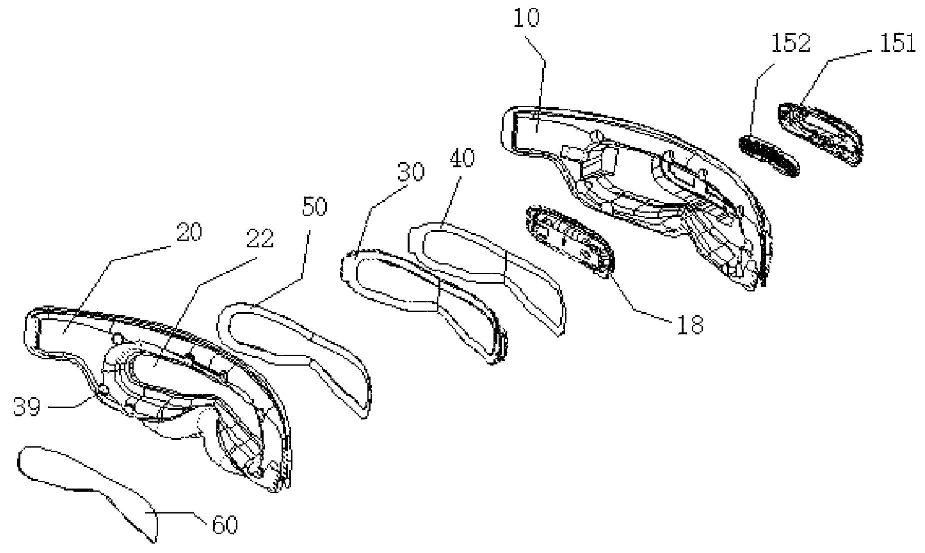
FIG. 4 is a partial exploded view of the eye mask according to the embodiment of the present invention.
Figure 5:
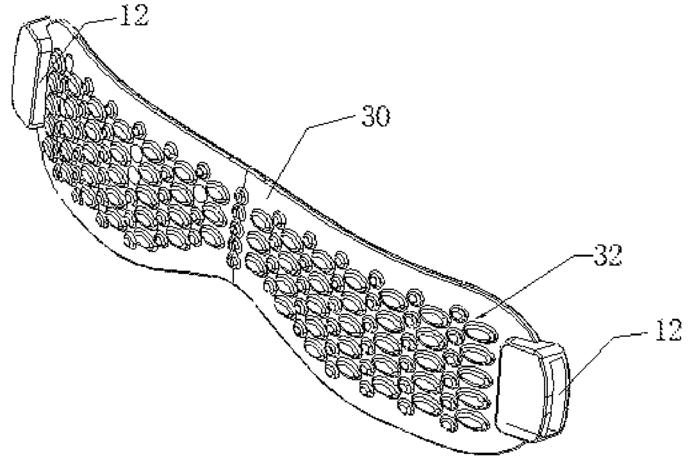
FIG. 5 is a light guide plate of the eye mask according to the embodiment of the present invention.

In particular, in order to prevent the light emitted by the first illuminants 12 from being too strong or overheated for the eyes, see FIGS. 3-5, the casing 11 includes an outer casing 10 and an inner casing 20, and the two first illuminants 12 can be arranged on a light guide plate 30 which is located between the inner casing 20 and the outer casing 10. Specially, the inner casing 20 has a through hole 22, the light guide plate 30 has a plurality of light guide structures 32 formed thereon, and a light reflective component 40 is arranged adjacent to the light guide plate 30 to reflect the light to the through hole 22 of the inner casing 20. A light uniform cloth layer 60 is further provided on the inner surface of the through hole 22 of the inner casing 20, the light uniform cloth layer 60 can transmit light and also play a role in diffusing uniform light, making the light felt by the user's left and right eyes uniform and comfortable.

In present embodiment, the second information prompting device includes a second illuminant 13, and the second illuminant 13 is located on the outer surface 111 of the casing 11. The first illuminant 12 and the second illuminant 13 can both be LEDs, and the displayed color and light intensity can be designed through the control circuit of the circuit board, for example, in different working modes, different control circuits can be connected to give different displayed color and light intensity. Preferably, the two first illuminants 12 can be linked to emit light in some working modes. The situation of the linked lighting includes that one control circuit can turn on the two first illuminants 12 at the same time, or when one first illuminant 12 is turned on, it triggers the other first illuminant 12 to be turned on, then the two first illuminants 12 simultaneously issue information prompts according to a selected working mode.

Referring to FIG. 4, a plurality of massage vibrators 39 and a heat component 50 are also provided in the eye mask, so that the eye mask 100 has massage function and heat function. In particular, the massage vibrators 39 are arranged on the inner casing 20, and arranged according to the acupuncture points around the eyes. The heat component 50 is in a ring shape and arranged adjacent to the inner casing 20.

Referring FIG. 1 and FIGS. 3-4, the control button 15 of the first illuminant 12 and the second illuminant 13 can be arranged on the outer surface 111 of the casing 11, and the control button 15 is connected with a controller 18, which can be in the form of multiple buttons or one smart button to scroll the menu in the optimized mode. In present embodiment, the control button 15 includes a light transmitable housing 151 and a circuit board 152, the second illuminant 13 can be directly arranged on the circuit board 152, and the circuit board 152 is placed on the outer surface 111 of the casing 11, the second illuminant 13 emits light to the outside through the control button 15. In another embodiment, the second illuminant 13 may be exposed on the outer surface of the casing 11.

Please referring to FIG. 6 and FIG. 7, mode controls of a working state of the eye mask 100 of the present application can be various according to the combination of lights. For example, in the heat mode, the control method includes controlling both the two first illuminants 12 to emit red light, and the intensity of the light increases when the heat temperature increases. The temperature of the heat mode can be controlled by a temperature sensor so that the temperature will not be too high. As the heat temperature rises, the intensity of the light increases, so that the user can perceive the heat temperature is rising through the change of the intensity of the light of the internal first illuminant 12 even the eye mask covers the eyes.

In a massage mode, the control method includes controlling the brightness/intensity of the lights of both the two first illuminants 12 to change when the massage vibrator vibrates, for example, the two first illuminants 12 can have a bright light for a period of time, and have a dark light for another period of time. In a preferred embodiment, the respective durations of the brightness and darkness of the light can be consistent with the vibration frequency or a vibration pattern of the massage vibrator. The light pattern prompts the user he has entered the massage mode. In addition, alternating bright light and dark light help to relax the nerves. In one embodiment, the above bright light and the dark light of the two first illuminants 12 each can be 630 nm wavelength light, that is, the two eyes of the user perceive the same wavelength light, this in one aspect help reduce disturbance for the user to help go to sleep, in another aspect, the specific wavelength can stimulate melatonin secretion, generate drowsiness, and improve sleep.

In further another period of time, the two first illuminants 12 can emit different wavelength light, respectively, for example, one of the first illuminants 12 can emit 590 nm wavelength light, the other one of the first illuminants 12 cam emit 630 nm wavelength light, such that the two eyes of user can perceive different lights, this help awake the user. Alternatively, the two first illuminants 12 each can alternatively change between 590 nm and 630 nm wavelength light, such alternatively change pattern also cause different lights for the eyes of the user, and the different lights for the two eyes cause stimulation of the left and right brain, thus help the user focuses on a work, i.e, he may have more concentration.

When the working mode of the working state of the eye mask 100 changes, the control circuit that the two first illuminant 12 flash in tandem can be triggered first, so that the two first illuminants 12 can flash in tandem to remind the user. In a weak power mode, the eye mask 100 can also control one of the first illuminant 12 to flash to remind the user, and at this time, the other first illuminant 12 maintain the original working parameters, that is, the first illuminants 12 can work simultaneously, but issue different information prompts.

The eye mask 100 can also have other working modes, such as the breathing guidance working mode, in this working mode, the light can be controlled to alternate between the first intensity and the second intensity, and the user adjusts breathing according to the intensity of the light. This breathing guidance working mode can be combined with the above massage mode.

The eye mask 100 can also have a meditation work mode, on which meditation music can be loaded, or favorite meditation music can be loaded by connecting an external communication device. The control method also includes when the eye mask is in the meditation work mode, controlling the first illuminant 12 and the second illuminant 13 flash with red light to remind the user that they are in meditation mode, and the user can still perceive the flashing red light waves with slightly closed eyes. In the meditation working mode, the user can wear earplugs 16. In addition the entire eye mask can have a fixing strap 17 to facilitate the user to wear the eye mask fixedly without falling off when the casing 11 covers the eyes of the user.

In a communication associated working mode, the control method further includes controlling the two first illuminants 12 to emit blue light waves and flash to remind the user when new information comes from the communication device.

More intelligently, the eye mask can have a working state time setting, or can be connected to the alarm clock setting on the communication device, and when the time is over, the two first illuminants 12 are controlled to display in a predetermined color and flash a predetermined number of times and/or the light intensity gradually changes from dark to strong to remind the user, so that the user perceives or wakes up gradually.

The above-mentioned eye mask, together with its control method is to use the external information prompting device to remind others, for example, public people that the user wearing the eye mask is in a certain working state, for example, he may be doing breathing physiotherapy, meditation, etc. or simply massage or hot compress state, and use the internal information prompting device to remind the user himself what working state the eye mask is in, and the external information prompt and the internal information prompt work at the same time, so the eye mask interacts with others or the user himself. The eye mask of the present invention meets people's control needs such as humanization and intelligence by using light combination.

In a preferred embodiment, the types of the first information prompting device and the second information prompting device are the same, for example, if the first information prompting device is a light, the second information prompting device is also a light.

In another preferred embodiment, the first information prompting device is a liquid crystal display facing the user wearing the eye mask, and the second information prompting device is a projection screen facing public, the types of first and second information prompting devices are basically the same, and the information prompts given by or the content displayed by the first and second information prompting devices can be simultaneously related. The related information prompts or content preferably refers to the same information prompts or content display on the liquid crystal display and the projection screen. With this above configuration, it is suitable for AR deep meditation guided teaching for multi-students, with what the teacher sees is the same as what meditation the students see, and in this situation, the meditation mode can be combined with the above-mentioned heat mode, breathing guidance mode, massage mode, weak current mode, and communication association mode, and teachers and students can experience the same meditation, breathing, physical therapy, etc.

Please referring to FIG. 8, a further mode control of the working state of the eye mask 100 of the present application can be varied according to the color and intensity of the light. The control method includes controlling the intensity and/or color of the light emitted by the first illuminants 12 to change and present a periodic change rule, the change rule being associated with the vibration rule of the massage vibrator.

In one working mode, the control method includes controlling the two first illuminants 12 to have a first light intensity and a second light intensity greater than the first light intensity, and to exhibit a change rule between the first light intensity and the second light intensity. Every time of the first light intensity changing to the second light intensity, the vibration function of the massage vibrator is turned on, and when the second light intensity changes to the first light intensity, the stop function of the massage vibrator is turned on. In a preferred embodiment, the first light intensity is relatively dark, and the second light intensity is relatively bright, every time it changes from dark to bright, the vibration function of the massage vibrator is in the on state, and the on state can be applied with gradually increasing the massage force, or maintaining a uniform massage force after it is turned on, or the massage mode of the massage vibrator, such as grasping, kneading and rotating, etc. Every time it changes from bright to dark, the stop function of the massage vibrator is in the on state, and the on state can be applied with a working parameter that gradually reduces the massage force, or to turn it off all at once. The alternation of the light from dark to bright and from bright to dark can prompt the user to enter the sleep state, and it is associated with the vibration pattern of the massage vibrator so that the user perceives that the working state of the eye mask is repeated, so that the user can adjust his breathing rhythm, thereby gradually fall asleep.

The control method further includes controlling the two first illuminants 12 to maintain the first light intensity and/or the second light intensity for a predetermined time, and the first light intensity and/or the second light intensity are maintained during the maintenance period. During the maintenance period of the first light intensity and/or the second light intensity, the massage vibrator can remain the same working parameters, such as massage strength, massage mode, etc., so that can increase the adaptation time for the user.

In another working mode, the control method further includes controlling the colors of the light emitted by the two first light illuminants 12 to change from red, orange, yellow, green, blue, blue, and purple, and the order of orange, yellow, green, blue, blue and purple presents a periodic change rule. The colors of the light emitted by the two first illuminants 12 at the same time can be the same or different. In a preferred embodiment, the light emitted by the first illuminants 12 is in the change cycle of red, orange, yellow, green, blue, blue, and purple, at this time, the vibration function of the massage vibrator is turned on and in a adjacent next change cycle of red, orange, yellow, green, blue, blue, and purple, the stop function of the massage vibrator is turned on. The activation of the vibration function and the activation of the stop function may be a manner in which the application gradually increases and decreases the massage intensity. The periodic change of the light color also makes the user perceive its regularity, which helps to relax oneself into a sleep state.

In another embodiment, the control method can control a change period of the light emitted by the two first light emitters 12 in red, orange, yellow, green, blue, blue and purple, the vibration and stop of the massage vibrator repeat alternatively. For example, a change period time of the red, orange, yellow, green, blue, blue and purple is 1 minute, and in this 1 minute, each vibration of the massage vibrator lasts for 10 seconds and stops for 2 seconds, so that in one cycle, the vibration and stop of the massage vibrator repeat 5 times.

The above-mentioned control method can set the working time of the above-mentioned working mode, for example, it can be executed for 10 minutes, and the above-mentioned working law can be repeatedly executed within the set time, and even the color and intensity of the light of the illuminant can be combined.

When there is a heat component, and when the working law of the heat component is associated with to the work law of the two first illuminants 12, the working law of the heat component can be that the heat mode is turned on and the heat mode is stopped, and when the heat mode is turned on, it can also be gradually heated, and when the heat mode is stopped, it can be gradually cooling, and a longer duration of the heat on and shorter duration of the stop working pattern. In another embodiment, the heat component may not be associated with the working law of the two first illuminants 12, that is, not be associated with the working law of the massage vibrator, but operate independently, for example, during the entire working period of the eye mask, the heat component can be kept open, and it utilizes the temperature sensor to perform temperature automatic adjustment control.

The above-mentioned eye mask is to use the law of the lighting module to be associated with the working law of the massage module and/or the hot module, and can give the user information prompts that a certain state is in progress, so as to guide the user to relax psychologically, and the user can also use this law to adjust breathing. This can help the user sleep, or help the user enter a meditative state, which is good for helping the user sleep.

The above-mentioned control program can be executed by using different functional modules on the controller, and the eye mask is more intelligent because of the controller.

The above description does not limit the present invention in any form. Although the present invention has been disclosed by the above-mentioned embodiments, it is not intended to limit the present invention. When the technical content disclosed above can be used to make some changes or be modified into equivalent embodiments with equivalent changes, but if they do not deviate from the content of the technical solution of the present invention, any simple modifications made to the above embodiments according to the technical essence of the present invention, are equivalent to changes and modifications all still belong to the scope of the technical solution of the present invention.

What is claimed is:

1. An eye mask, comprising:

a casing;

a first information prompting device and a second information prompting device arranged on the casing, the first information prompting device configured for internally giving information prompts, the second information prompting device configured for externally giving information prompts; and a controller configured for controlling the first information prompting device and the second information prompting device to give information prompts simultaneously in a working state;

wherein the first information prompting device is a liquid crystal display configured to face a user wearing the eye mask, the second information prompting device is a projection screen configured for public viewing, and the information prompts given by the first information prompting device and the information prompts given by the second information prompting device are the same.

2. The eye mask according to claim 1, wherein the first information prompting device comprises two first illuminants located in an inner surface of the casing, symmetrically distributed on both sides of the casing and substantially corresponding to positions of eyes of a user.

3. The eye mask according to claim 2, wherein the two first illuminants are arranged on a light guide plate, and the two first illuminants are connected to different circuits of the controller.

4. The eye mask according to claim 2, further comprising a heat component and a massage vibrator arranged in the casing, the two first illuminants emit red light when the heat component works, and an intensity and/or a color of a light emitted by the two first illuminants changes according a periodic change rule related to a working rule of the massage vibrator.

5. A control method of the eye mask of claim 1, comprising:

controlling the first information prompting device and the second information prompting device to give information prompts simultaneously; and controlling the first information prompting device and the second information prompting device to give the same information prompts.

6. The control method according to claim 5, wherein the first information prompting device comprises two first illuminants located in an inner surface of the casing, symmetrically distributed on both sides of the casing and substantially corresponding to positions of eyes of a user, the control method comprises controlling the two first illuminants to emit light simultaneously.

7. The control method according to claim 6, wherein the eye mask comprises a heat mode with a heat component, and the control method further comprises controlling the two first illuminants to emit red light when the eye mask is in the heat mode, and an intensity of the light increases when a heat temperature increases.

8. The control method according to claim 6, wherein the eye mask comprises a weak power mode, the control method comprises controlling one of the first illuminants to flash to remind the user when the eye mask is in the weak power mode, while the other one of the first illuminants maintains working parameters thereof.

9. The control method according to claim 6, wherein the eye mask comprises a breathing guidance mode, the control method comprises controlling the two first illuminants to simultaneously emit a light with a first intensity and alternatively simultaneously emit a light with a second intensity in the breathing guidance working mode.

10. The control method according to claim 6, wherein the eye mask comprises a massage mode with a massage vibrator, the control method comprises controlling an intensity and/or a color of the light emitted by the two first illuminants to change, and to present a periodic change rule related to a working rule of the massage vibrator.

11. The control method according to claim 10, wherein in the massage mode, the control method comprises controlling both the two first illuminants to emit 630 nm wavelength light in a first period of time, and controlling one of the first illuminants to emit 590 nm wavelength light, and the other one of the first illuminants to emit 630 nm wavelength light in a second period of time.

12. The control method according to claim 6, wherein the eye mask comprises a communication associated mode, and the control method comprises controlling the two first illuminants to emit blue light and flash to remind the user when new information comes from a communication device.

13. The control method according to claim 6, wherein the eye mask comprises a meditation mode, and the first information prompting device includes a first illuminant, the second information prompting device includes a second illuminant, the control method comprises controlling the first illuminant and the second illuminant to both flash red light.

14. The control method according to claim 6, wherein the control method comprises setting a working time for a working mode of the eye mask, and when the working time is over, controlling the two first illuminants to display in a predetermined color, or flashing a predetermined number of times or giving light intensity gradually changing from dark to bright to allow the user to be prompted.

15. An eye mask, comprising:

a casing;

an internal information prompting device and an external information prompting device arranged on the casing, the internal information prompting device configured for giving information prompts for a user wearing the eye mask, the external information prompting device configured for giving information prompts for public viewing; and a controller configured for controlling the internal information prompting device and the external information prompting device to give the same information prompts simultaneously.

* * * * *